United States Patent
Schiff et al.

(10) Patent No.: US 9,597,455 B2
(45) Date of Patent: Mar. 21, 2017

(54) SYRINGE HAVING A SPRING ACTION PLUNGER ROD

(71) Applicant: Becton Dickinson France, S.A.S., Le Pont-de-Claix (FR)

(72) Inventors: David Robert Schiff, Highland Park, NJ (US); Mathieu Dominic Turpault, Pennington, NJ (US); Antonio Gatta, Philadelphia, PA (US); John Depler Coleman, Philadelphia, PA (US)

(73) Assignee: Becton Dickinson France S.A.S., Le Pont-de-Claix (FR)

( * ) Notice: Subject to any disclaimer, the term of this patent is extended or adjusted under 35 U.S.C. 154(b) by 351 days.

(21) Appl. No.: 13/622,380

(22) Filed: Sep. 19, 2012

(65) Prior Publication Data
US 2013/0085457 A1 Apr. 4, 2013

Related U.S. Application Data

(60) Provisional application No. 61/541,618, filed on Sep. 30, 2011.

(51) Int. Cl.
*A61M 5/315* (2006.01)
*A61M 5/31* (2006.01)

(52) U.S. Cl.
CPC ...... *A61M 5/31511* (2013.01); *A61M 5/3135* (2013.01); *A61M 5/31501* (2013.01); *A61M 2005/31518* (2013.01)

(58) Field of Classification Search
CPC ............ A61M 5/2033; A61M 5/31505; A61M 5/31511; A61M 5/31515; A61M 5/3272; A61M 2005/31518; A61M 5/31501; A61M 5/3135

USPC ....... 604/131, 134, 135, 210, 223, 195, 198, 604/219
See application file for complete search history.

(56) References Cited

U.S. PATENT DOCUMENTS

| | | | |
|---|---|---|---|
| 4,333,456 A | 6/1982 | Webb | |
| 4,636,202 A | 1/1987 | Lowin et al. | |
| 2002/0004648 A1* | 1/2002 | Larsen et al. | 604/195 |

(Continued)

FOREIGN PATENT DOCUMENTS

| WO | 2009/108847 A1 | 9/2009 |
|---|---|---|
| WO | 2009/108869 A1 | 9/2009 |

*Primary Examiner* — Laura Bouchelle
*Assistant Examiner* — Justin L Zamory
(74) *Attorney, Agent, or Firm* — The Webb Law Firm

(57) ABSTRACT

A syringe assembly including a syringe barrel defining a chamber having a stopper therein is disclosed. The syringe assembly includes a plunger rod associated with the stopper, the plunger rod includes an outer sleeve having a distal end interconnected to the stopper and a sidewall portion defining an opening therein. The plunder rod also includes an inner sleeve disposed within the outer sleeve including a longitudinally extending track in alignment with the opening in the outer sleeve. The inner sleeve is adapted for telescopic movement with respect to the outer sleeve. The plunger rod also includes a spring mounted in association with the inner sleeve. The syringe assembly further includes a holding mechanism associated with the plunger rod and configured for cooperation with the inner and outer sleeves. Relative movement between the inner and outer sleeves causes the plunger rod to transition from a collapsed position to an extended position.

18 Claims, 13 Drawing Sheets

(56) References Cited

U.S. PATENT DOCUMENTS

| | | |
|---|---|---|
| 2006/0276755 A1 | 12/2006 | Sullivan et al. |
| 2008/0167611 A1* | 7/2008 | Miller .......................... 604/110 |
| 2010/0081997 A1* | 4/2010 | Moed ..................... A61M 5/24 |
| | | 604/191 |
| 2011/0196313 A1* | 8/2011 | Mudd .......................... 604/219 |

* cited by examiner

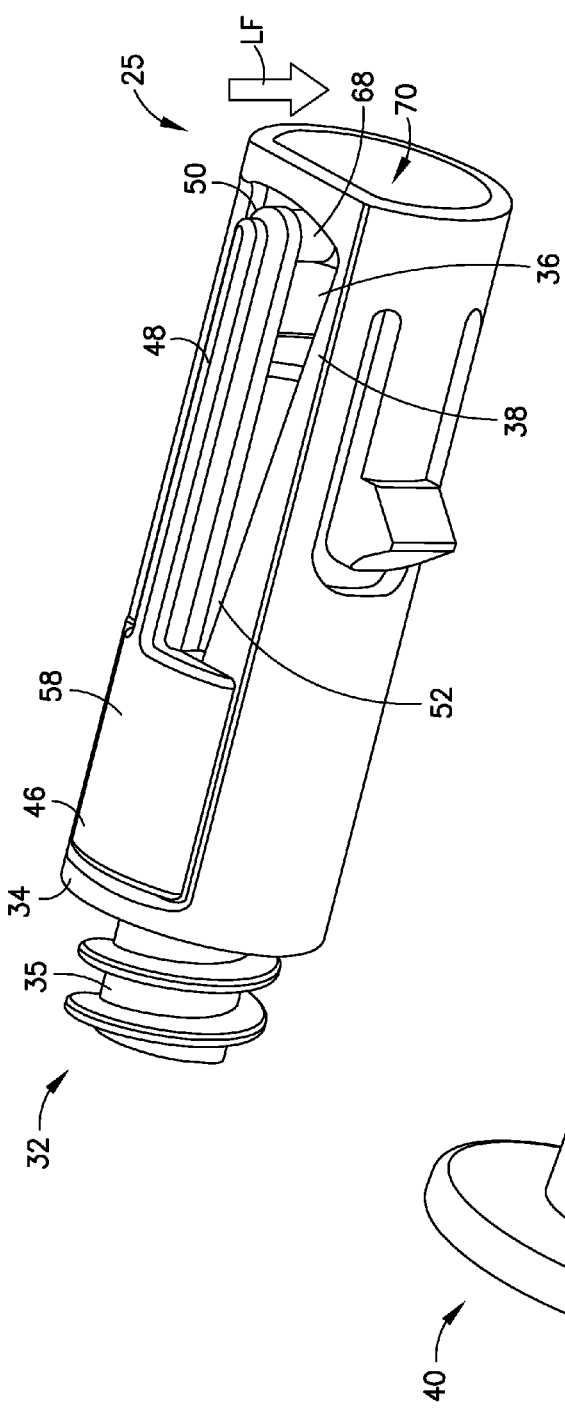
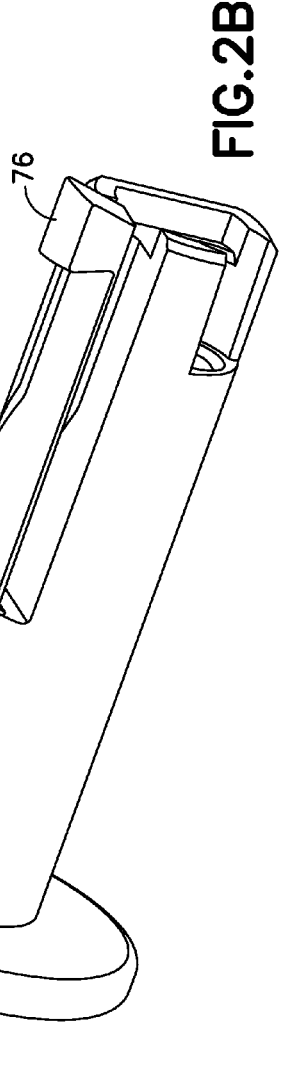
FIG.2A
FIG.2B

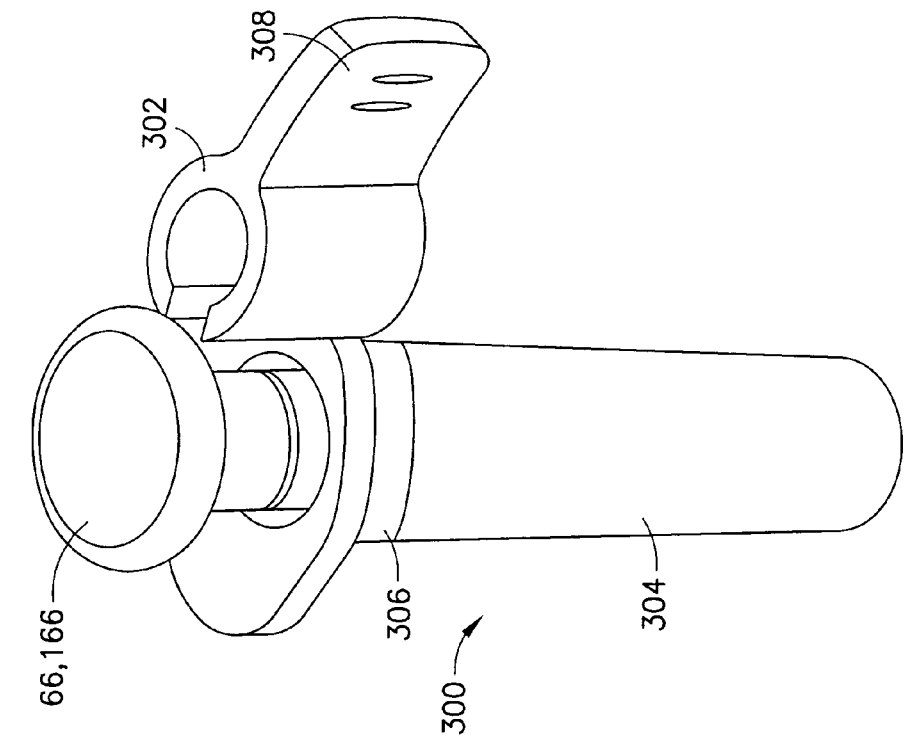
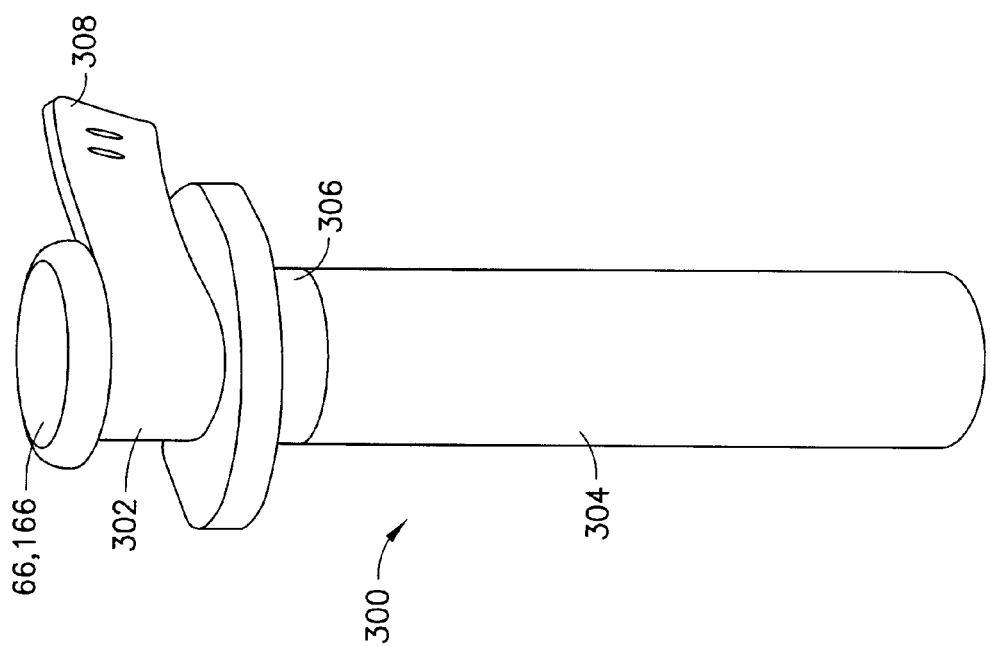
FIG. 8B
FIG. 8A

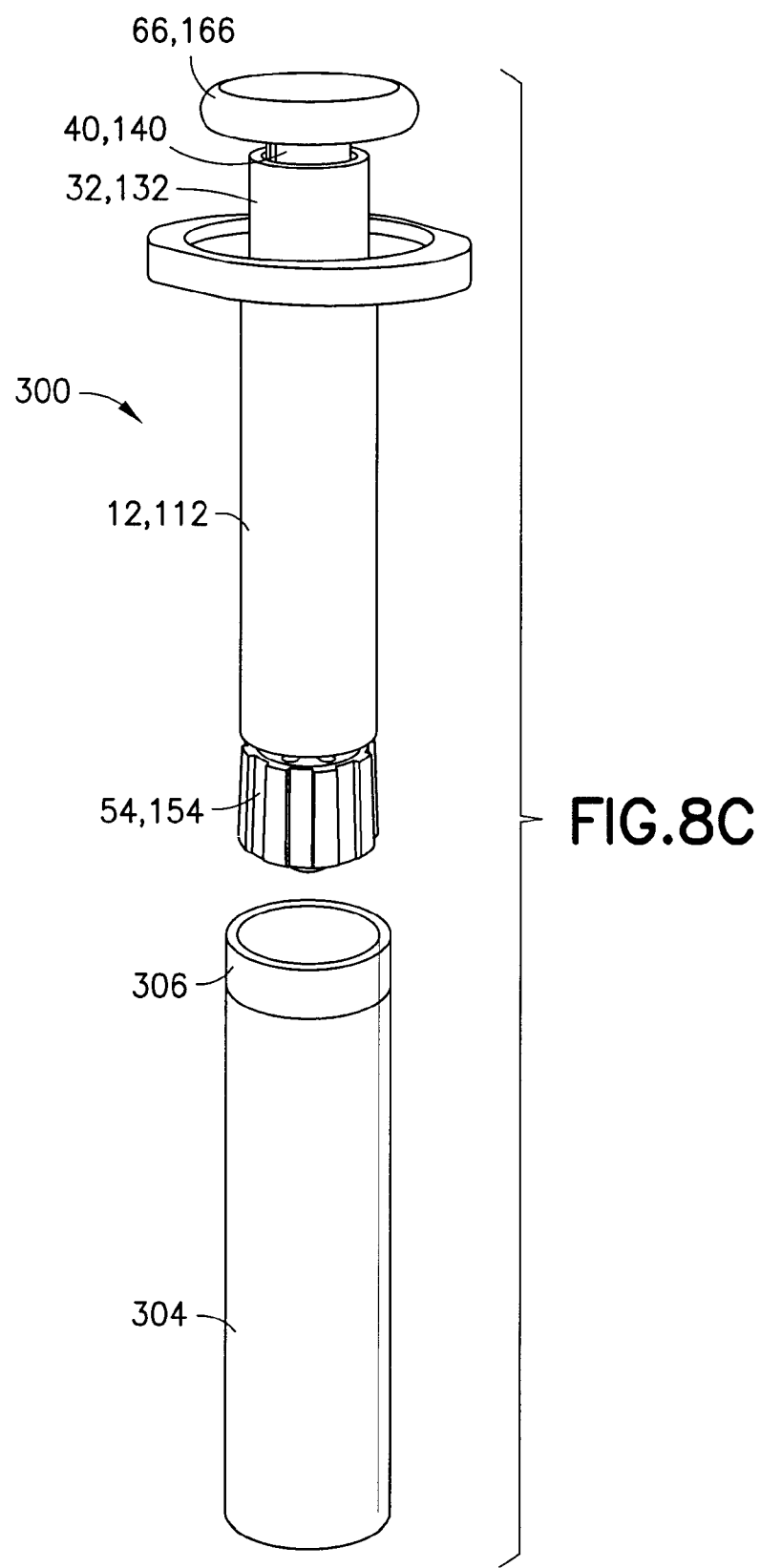

SYRINGE HAVING A SPRING ACTION PLUNGER ROD

CROSS-REFERENCE TO RELATED APPLICATION

This application claims priority to U.S. Provisional Application Ser. No. 61/541,618 filed Sep. 30, 2011, the entire disclosure of which is hereby incorporated by reference.

BACKGROUND OF THE INVENTION

Field of the Invention

The present invention is directed to a pre-filled syringe assembly adapted for the dispensing and delivery of a fluid. More particularly, the present invention is directed to a pre-filled syringe assembly having a spring actuated plunger rod resulting in a smaller packaging footprint allowing for reduced storage space. The present invention is also directed to a packaging system for a pre-filled syringe assembly that prevents unintended actuation of the plunger rod and reduces the likelihood of tampering of the syringe contents.

Description of Related Art

Conventional syringes are well known to be used in connection with a vial of a medication, where the user draws the fluid into the syringe immediately prior to injection and delivery of the fluid to the patient. A conventional syringe typically includes a syringe barrel with an opening at one end and a plunger mechanism disposed through the other end. The plunger typically includes a plunger rod extending through the barrel, with a plunger head or stopper at the end of the plunger rod within the barrel and with a finger flange at the other end of the plunger rod extending out of the barrel. In use, the plunger rod is retracted through the syringe barrel to fill the syringe barrel with a fluid, such as a medication, with the plunger rod extending out from the rear end of the syringe barrel. For delivery of the medication to a patient, the opening of the syringe barrel is adapted for fluid communication with a patient, such as through a hypodermic needle fitted at the front end of the syringe barrel or through a luer-type fitting extending from the front end of the syringe barrel for attachment with a fluid line of a patient. Upon depression of the plunger rod, the plunger rod and stopper travel through the syringe barrel, thereby forcing the contents of the syringe out through the opening at the front end for delivery to the patient. Such an operation is well known in the medical field, and medical practitioners have become well accustomed to the use of such common fluid delivery procedures through standard syringes.

Oftentimes, hypodermic syringes may be packaged as "pre-filled" devices, wherein the syringe is pre-filled with medication prior to being packaged and delivered to the end user. In this manner, there is no need for the user to fill the device prior to injection, thereby saving time for the end user and maintaining consistent volumes for delivery. Pre-filled syringes and pre-filled metered dose syringes are often filled with narcotics or other drugs at a production facility, packaged, and then shipped to a medical facility. Once at the facility, these syringes are often placed in controlled storage and/or locked cabinets to reduce theft of the syringes themselves and/or theft of the contents of these syringes. The space within these controlled storage locations is often limited, thus there is a need for a syringe assembly that has a smaller packaging footprint, to reduce the storage space required for containing this syringe. It is also desirable to produce syringes that are uniform in terms of an outer surface shape to allow for stacking of the syringes within the storage cabinet.

Even though measures, such as controlled storage, are taken to ensure the contents of these syringes remain intact, the risk still remains that the syringe contents can be tampered with and/or stolen and replaced with a saline solution. One technique for preventing tampering is the use of a snap cap for the tip cap that makes a snapping noise when removed from the syringe assembly. For example, a tamper-proof cap for a pre-filled syringe including a top member concentrically disposed in a generally cylindrical sleeve member and connected by frangible elements to the sleeve member is conventionally known. In addition, it is known to include an outer cap for a pre-filled syringe that is covered with a cylindrical cover cap which connects with the top wall of a holding member through a frangible portion. The cylindrical cover cap may be broken from the top wall of the holding member for tampering prevention/tamper-proof evidence.

SUMMARY OF THE INVENTION

In accordance with an embodiment of the present invention, a syringe assembly includes a syringe barrel having a first end, a second end, and a sidewall extending between the first end and the second end defining a chamber. The syringe assembly also includes a stopper disposed within the chamber of the syringe barrel. The syringe assembly further includes a plunger rod associated with the stopper, the plunger rod having an outer sleeve having a distal end interconnected to the stopper, the outer sleeve including a sidewall portion defining an opening therein, and an inner sleeve disposed within the outer sleeve, the inner sleeve including a longitudinally extending track, at least a portion of the track being in alignment with an opening in the outer sleeve. The inner sleeve is adapted for telescopic movement with respect to the outer sleeve. The plunger rod also includes a spring mounted in association with the inner sleeve. The syringe assembly further includes a holding mechanism associated with the plunger rod and configured for cooperation with the inner and outer sleeves, wherein relative movement between the inner sleeve and the outer sleeve causes the plunger rod to transition from a collapsed pre-use position to an extended ready-to-use position.

The relative movement between the inner and outer sleeves, such as by a distally directed force applied to the plunger rod, causes relative movement between the inner and outer sleeves to release the spring from a compressed position and transitions the plunger rod to the ready-to-use position. In the present invention, the plunger rod is transitionable from a pre-use position, in which the spring is in a compressed position and the inner sleeve is collapsed within the outer sleeve, and a ready-to-use position in which the spring is expanded and the inner sleeve is extended out from the outer sleeve.

In certain configurations, the opening in the outer sleeve has a longitudinally extending opening and the holding mechanism includes a flexible finger associated with the outer sleeve and the longitudinally extending opening. The holding mechanism can be a separate member that is secured to the outer sleeve or it can be integrally formed with the outer sleeve. The flexible finger can include a laterally extending member that is configured for cooperation with the opening in the outer sleeve and with the track in the inner sleeve, and the distally directed force applied to the inner sleeve causes relative movement between the laterally extending member and the track to release the spring from the compressed position and allow the inner sleeve of the plunger rod to transition from the collapsed pre-use position to the extended ready-to-use position. The longitudinally extending track can extend through a sidewall portion of the inner sleeve and the track can include a first stop and a second stop. The distally directed force causes disengagement of the laterally extending member from the first stop and release of the spring. This disengagement results in proximal movement of the inner sleeve with respect to the outer sleeve from the collapsed pre-use position to the extended ready-to-use position. Upon release and expansion of the spring, the laterally extending member moves along the longitudinally extending track and locks in the second stop to maintain the inner sleeve in the ready-to-use position. The flexible finger can be configured to flex in a lateral direction with respect to the longitudinally extending track, and the opening in the outer sleeve can be configured to disengage the laterally extending member from the first stop and engage the second stop upon release and expansion of the spring.

In the syringe assembly, the inner sleeve can include a locking finger configured for cooperating with an aperture in the outer sleeve, for locking the plunger rod in the extended ready-to-use position, and for preventing pull-out of the inner sleeve from the outer sleeve.

The syringe assembly can also include a stop member associated with the outer sleeve and configured to cooperate with the syringe barrel to limit movement of the outer sleeve into the syringe barrel upon the application of the distally directed force to the plunger rod. This feature can comprise a flex finger that prevents the application of a partial dose from a pre-filled syringe as it prevents the depression of the outer sleeve into the syringe barrel until expansion of the inner sleeve with respect to the outer sleeve.

The syringe assembly can include an alignment member associated with at least one of the inner sleeve and the outer sleeve to prevent relative rotation of the inner sleeve with respect to the outer sleeve. According to one design, the alignment member can comprise a keyed track.

In another configuration, the holding mechanism can comprise a spring finger and a U-shaped locking member cooperating with the outer sleeve and the longitudinally extending track of the inner sleeve. In a further configuration, the syringe assembly may include a medication or drug disposed within the syringe barrel.

In accordance with another embodiment of the present invention, a spring released plunger rod assembly for use with a syringe assembly includes an outer sleeve having a first end configured for interconnecting to a stopper, the outer sleeve including an opening extending through a sidewall portion. The plunger rod assembly includes an inner sleeve disposed within the outer sleeve and mounted for telescopic movement with respect to the outer sleeve, and a spring mounted in association with the inner sleeve. A longitudinally extending track is associated with the inner sleeve. The plunger rod assembly further includes a holding mechanism associated with a plunger rod and configured for cooperation with the inner and outer sleeves, wherein relative movement between the outer sleeve and the inner sleeve causes the plunger rod to transition from a collapsed pre-use position to an extended ready-to-use position.

In certain configurations, the holding mechanism comprises a flexible finger associated with the outer sleeve. The flexible finger can include a laterally extending member configured for cooperation with the opening in the outer sleeve and with the track in the inner sleeve and wherein the distally directed force applied to the inner sleeve causes relative movement between the flexible finger, the laterally extending member, and the track to release the spring from the compressed position and allow the inner sleeve of the plunger rod to transition from the collapsed pre-use position to the extended ready-to-use position. The longitudinally extending track can extend through a sidewall portion of the inner sleeve and can include a first stop and a second stop and wherein the distally directed force causes: disengagement of the laterally extending member from the first stop; release of the spring; and proximal movement of the inner sleeve with respect to the outer sleeve. Upon release and expansion of the spring, the laterally extending member locks in the second stop to maintain the inner sleeve in the ready-to-use position.

The inner sleeve of the plunger rod assembly can include a locking finger configured for cooperating with an aperture in the outer sleeve for locking the plunger rod in the extended ready-to-use position and for preventing pull-out of the inner sleeve from the outer sleeve. The plunger rod assembly can further include a stop member associated with the outer sleeve and configured to cooperate with a syringe barrel to limit movement of the outer sleeve into the syringe barrel upon the application of the distally directed force to the plunger rod.

In another configuration, the holding mechanism can comprise a spring finger and a U-shaped locking member cooperating with the outer sleeve and the longitudinally extending track of the inner sleeve.

In accordance with another embodiment, a packaging assembly for use with a pre-filled syringe assembly having a spring released plunger rod includes a cap configured for covering the plunger rod and a cover molded about a syringe barrel and a tip cap. The cover can be a tamper-indicating label and can be connected to the cap with a frangible portion. The cap can comprise a rigid member configured to prevent the application of a distally directed force on the plunger rod. In accordance with another configuration, the packaging assembly can include a tear tab positioned about a portion of the plunger rod at a location between a plunger rod thumb press and a syringe barrel flange. A cover can be molded about the syringe barrel and tip cap. The tear tab can include a grasping portion to assist in removal of the tear tab from about the plunger rod and can be configured to prevent distal movement of the spring released plunger rod and inadvertent release of the spring released plunger rod. The cover can include a tamper-indicating member. This tamper-indicating member can be in the form of a colored frangible attachment portion, wherein this frangible portion assists in the removal of the cover from about the syringe barrel and tip cap.

BRIEF DESCRIPTION OF THE DRAWINGS

FIG. 2A is a side perspective view of an outer sleeve of the plunger rod of FIG. 2 in accordance with an embodiment of the present invention.

FIG. 2B is a side perspective view of an inner sleeve of the plunger rod of FIG. 2 in accordance with an embodiment of the present invention.

FIGS. 8A-8C are perspective side views of a packaging assembly for the syringe assembly having a spring action plunger rod illustrating the operational steps for removal of the packaging assembly in accordance with an embodiment of the present invention.

DESCRIPTION OF THE PREFERRED EMBODIMENTS

Figure 1:
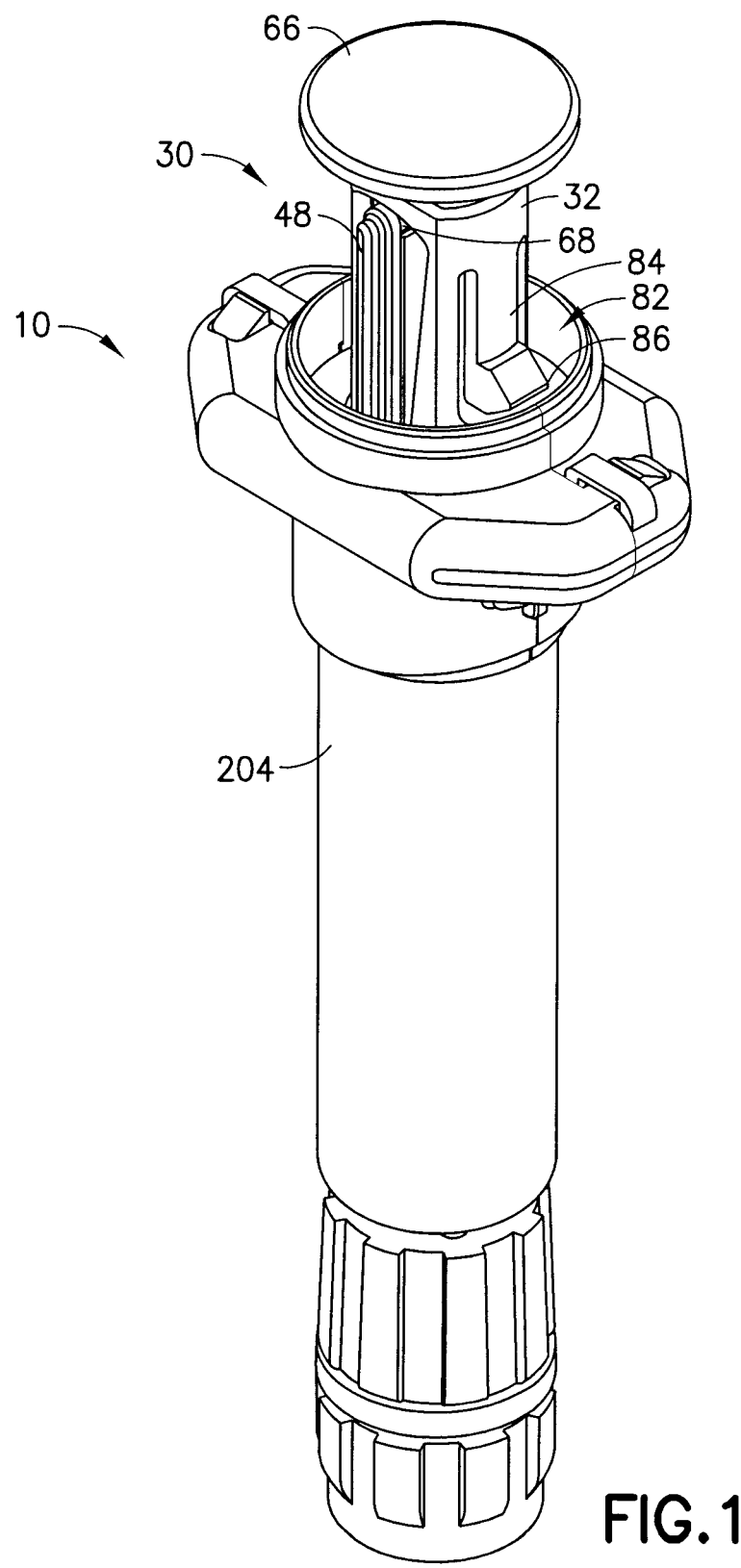
FIG. 1 is a front perspective view of a syringe assembly having a spring action plunger rod in a collapsed position in accordance with an embodiment of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Reference is now made to FIGS. 1, 1A, 2, 2A-2B, 3, 4A-4B, and 5A-5B which depict a syringe assembly according to an embodiment of the invention, generally indicated as 10, adapted for the dispensing and delivery of a fluid. FIGS. 6 and 6A-6B depict a syringe assembly according to a further embodiment of the invention, generally indicated as 100, which can also be adapted for the dispensing and delivery of a fluid. FIGS. 7 and 8A-8C depict differing packaging assemblies, generally indicated as 200 and 300, which can be used for packaging the syringe assembly of the invention.

Figure 1A:
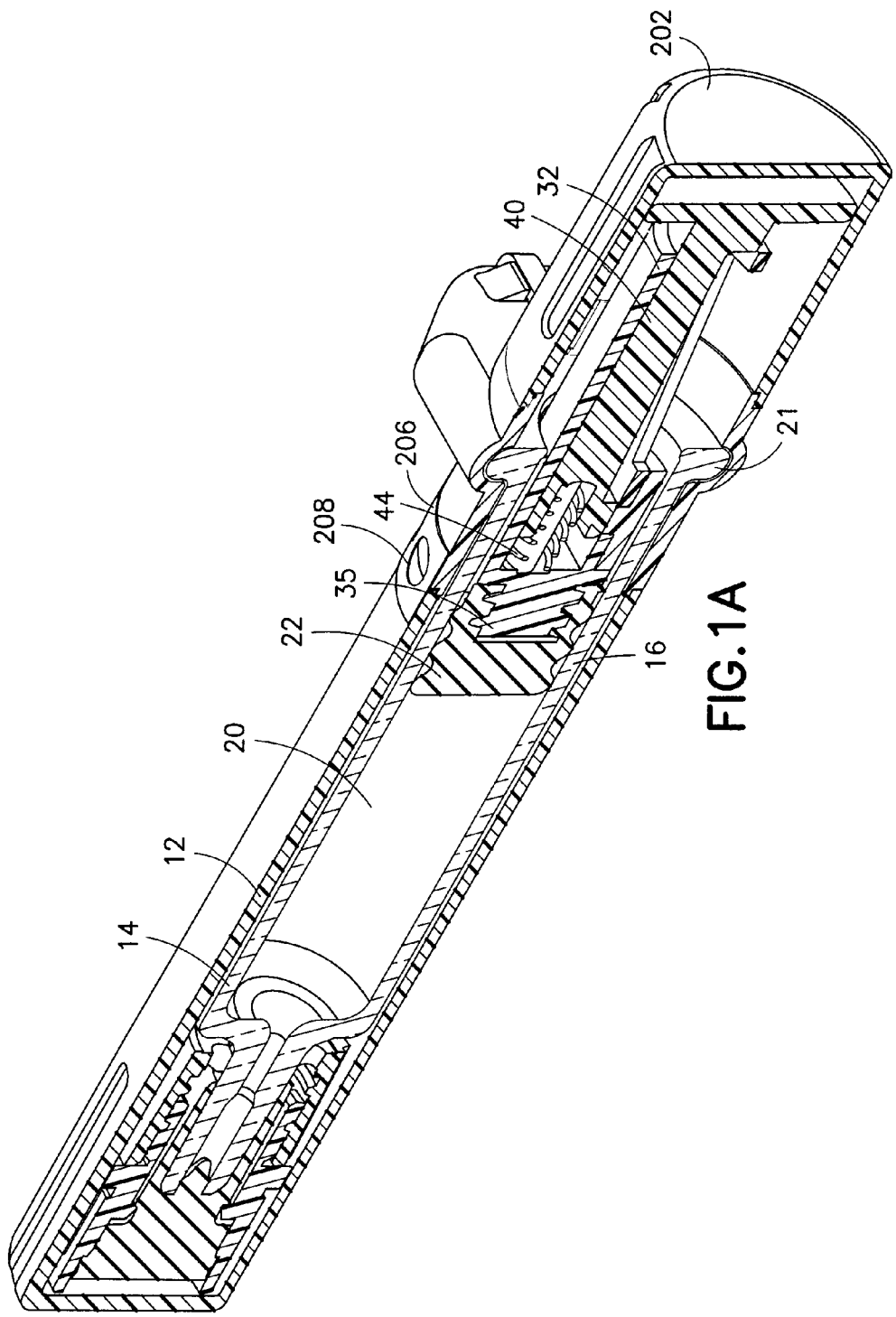
FIG. 1A is cross-sectional side perspective view of the syringe assembly of FIG. 1 in which the packaging components have been included in accordance with an embodiment of the present invention.
Figure 3:
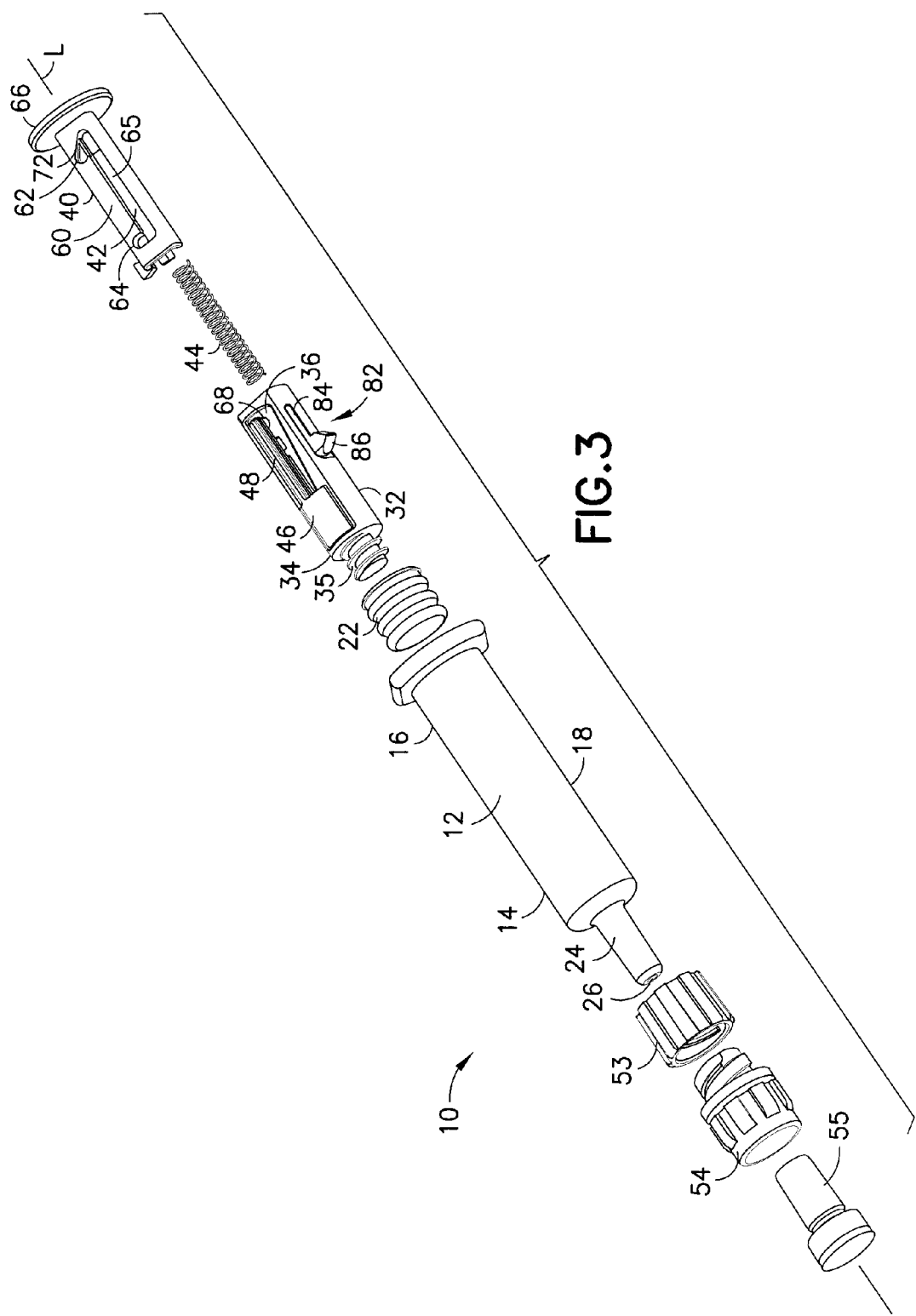
FIG. 3 is an expanded perspective view of the syringe assembly of FIG. 1 in accordance with an embodiment of the present invention.

With particular reference to FIGS. 1, 1A, and 3, the syringe assembly 10 is intended for use for injection or infusion of fluid, such as a medication, directly into a patient, and is generally shown and described for purposes of the present description as a hypodermic syringe. Syringe assembly 10 is contemplated for use in connection with a needle such as by connecting syringe assembly 10 to a separate needle assembly (not shown), or alternatively for connection with a separate intravenous (IV) connection assembly (not shown).

The syringe assembly 10 includes a syringe barrel 12 having a first or distal end 14, a second or proximal end 16, and a sidewall 18 extending between the distal end 14 and proximal end 16 defining an interior chamber 20 of the syringe barrel 12. A stopper 22 is slidably disposed within the chamber 20 of the syringe barrel 12. The syringe barrel 12 may be in the general form of an elongated cylindrical barrel as is known in the art for the general shape of a hypodermic syringe, although other forms for containing a fluid for delivery are also contemplated by the present invention. Additionally, the syringe barrel 12 may be formed of glass, or may be injection molded from thermoplastic material such as polypropylene and polyethylene according to techniques known to those of ordinary skill in the art, though it is to be appreciated that the syringe barrel 12 may be made from other suitable materials and according to other applicable techniques. In certain configurations, the syringe barrel 12 may include an outwardly extending flange 21 about at least a portion of the proximal end 16. The flange 21 may be configured for easy grasping by a medical practitioner, as will be discussed herein.

As illustrated in FIG. 3, the distal end 14 of the syringe barrel 12 terminates in a tip 24 having an outlet opening 26. The proximal end 16 is generally open-ended, but is intended to be closed off to the external environment, via the stopper 22, as will be discussed herein. According to one non-limiting embodiment, as shown in FIG. 3, the syringe assembly 10 can include a tip cap 54, an interface member 53 interfacing between the tip cap 54 and the tip 24 of the syringe barrel 12, and a plug 55, for sealing the outlet opening 26.

The syringe barrel 12 may include markings, such as graduations on the sidewall 18 thereof, for providing an indication as to the level or amount of fluid contained within the syringe barrel 12. Such markings may be provided on the external wall, the internal wall, or integrally formed or otherwise within the wall of syringe barrel 12. Alternatively, or in addition thereto, the markings may provide a description of the contents of the syringe, or other identifying information, as may be known in the art.

As noted, distal end 14 of syringe barrel 12 includes outlet opening 26. The profile of outlet opening 26 may be adapted for engagement with a separate dispensing device, such as a needle assembly or IV connection assembly, and therefore may include a mechanism for such engagement, for example, a generally tapered luer tip, for engagement with a separate tapered luer mating surface (not shown) or such a separate device for attachment therewith. In addition, a mechanism for locking engagement therebetween may also be provided, such as a luer collar or luer lock including interior threads. Such luer connections and luer locking mechanisms are well known in the art.

All of the components of syringe assembly 10 may be constructed of any known material, and are desirably constructed of medical grade polymers. As stated above, the syringe assembly 10 is particularly useful as a pre-filled syringe, and therefore may be provided for end use with a fluid, such as a medication, contained within interior chamber 20 of syringe barrel 12, pre-filled by the manufacturer. In this manner, syringe assembly 10 can be manufactured, pre-filled with a medication, sterilized, and packaged in appropriate packaging for delivery, storage, and use by the end user, without the need for the end user to fill the syringe with medication from a separate vial prior to use.

Figure 4A:
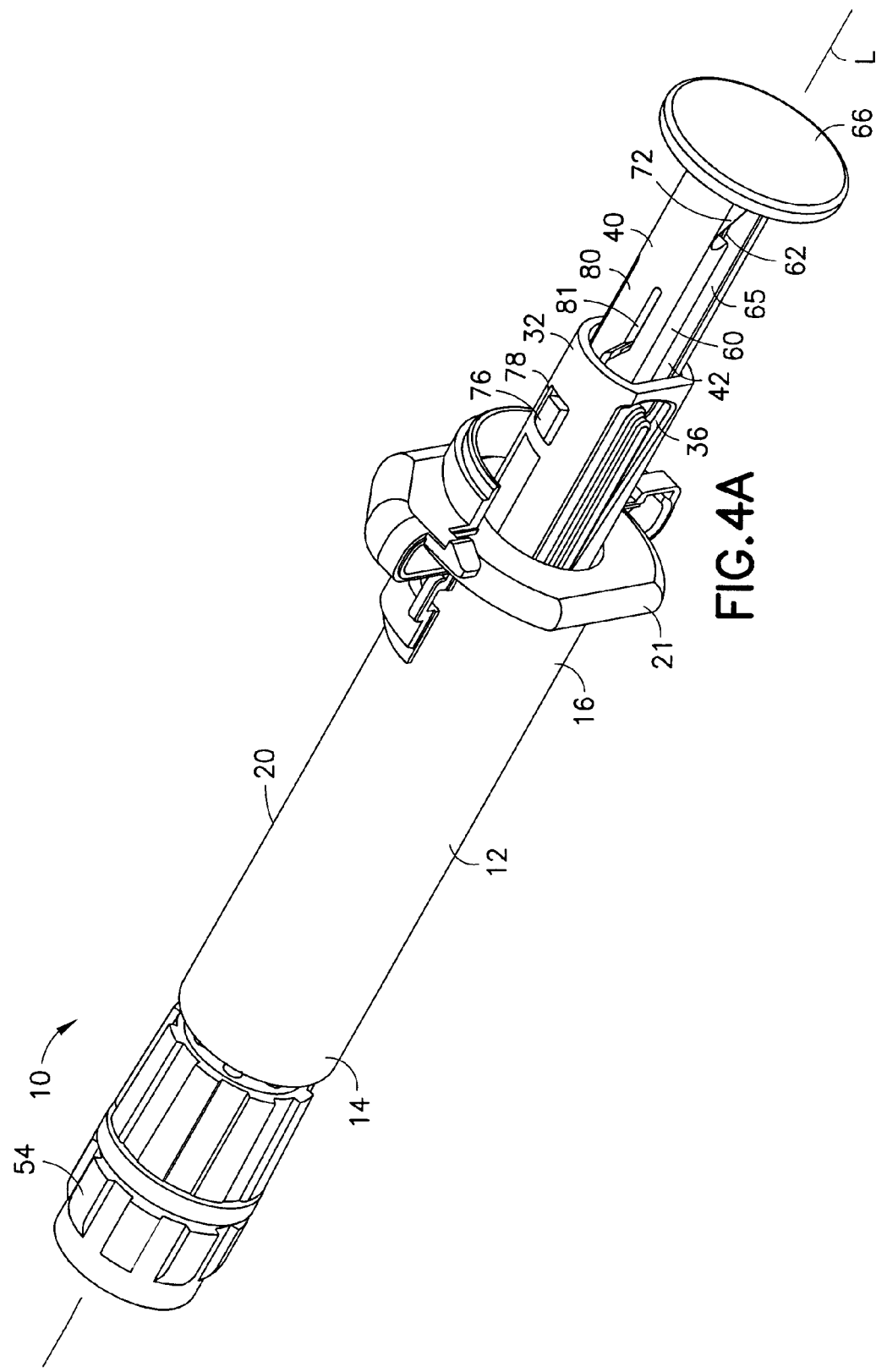
FIG. 4A is a side perspective view of the syringe assembly of FIG. 1 showing a locking flex finger in accordance with an embodiment of the present invention.
Figure 4B:
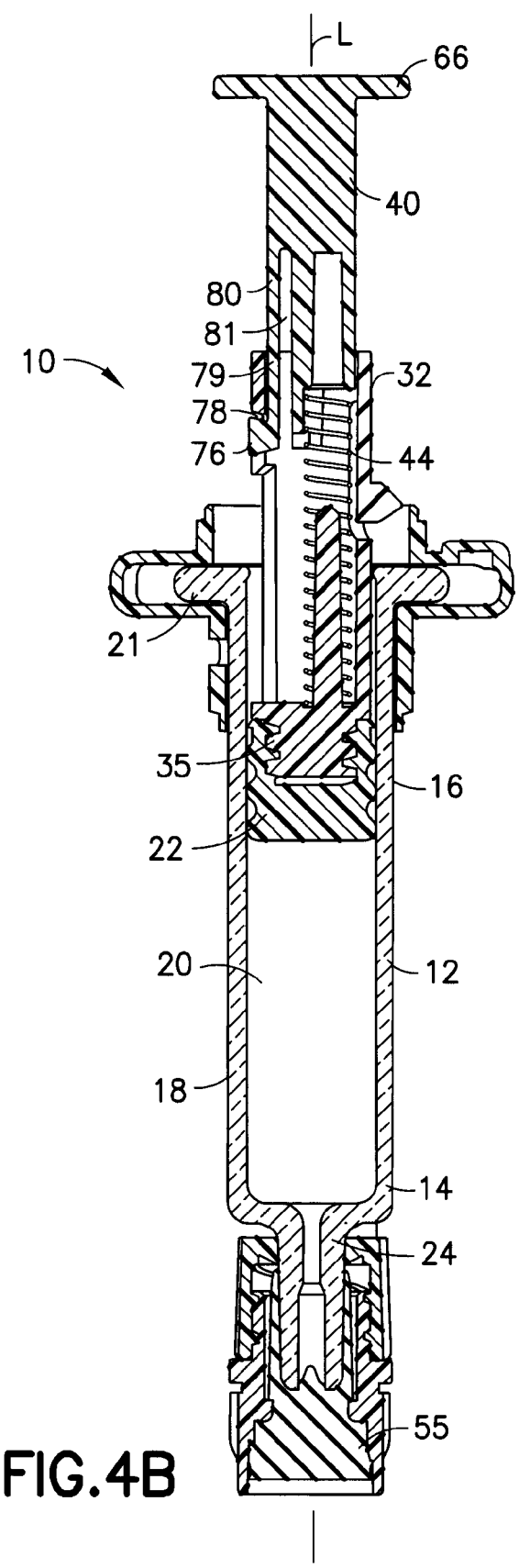
FIG. 4B is a cross-sectional view of the syringe assembly of FIG. 4A in accordance with an embodiment of the present invention.
Figure 5A:
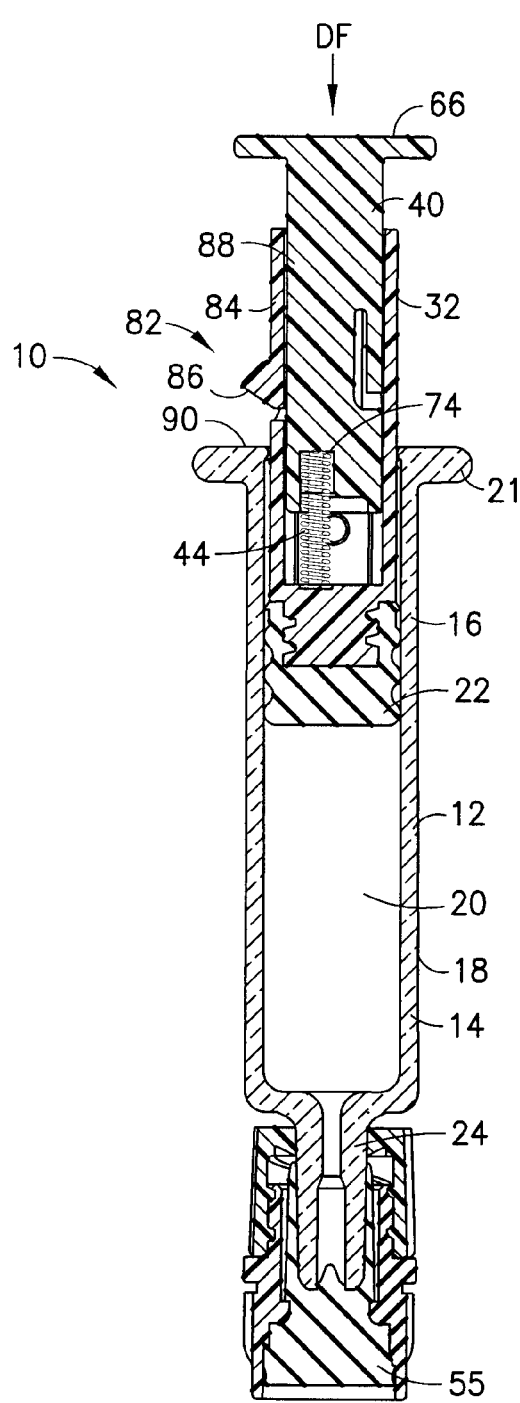
FIG. 5A is a cross-sectional view of the syringe assembly of FIG. 1 with the plunger rod in the collapsed position showing the partial dose prevention feature in accordance with an embodiment of the present invention.
Figure 5B:
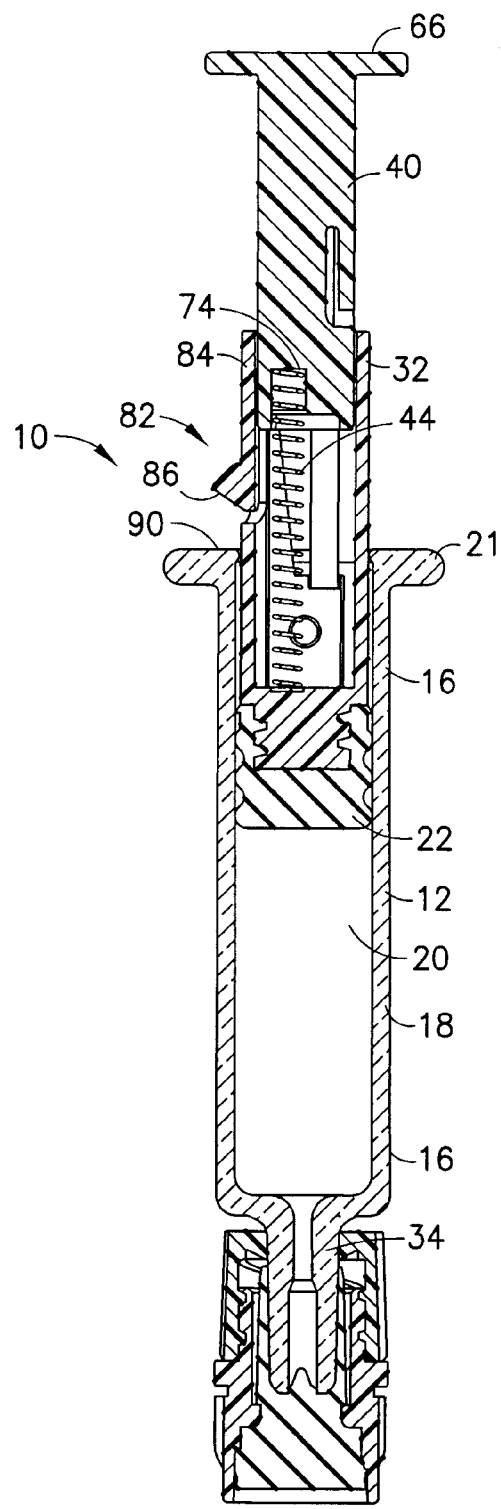
FIG. 5B is a cross-sectional view of the syringe assembly of FIG. 1 with the plunger rod in the extended position showing the partial dose prevention feature in accordance with an embodiment of the present invention.
Figure 6:
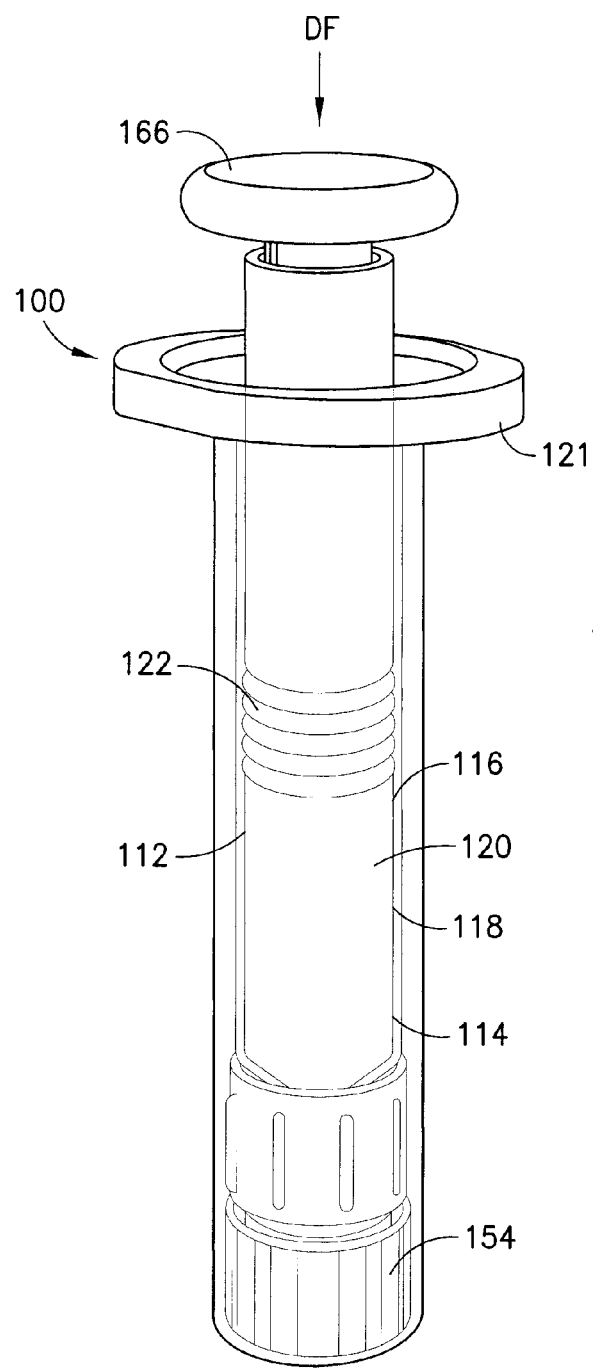
FIG. 6 is a front perspective view of the syringe assembly of the invention having a spring action plunger rod in a collapsed position in accordance with an embodiment of the present invention.
Figure 6B:
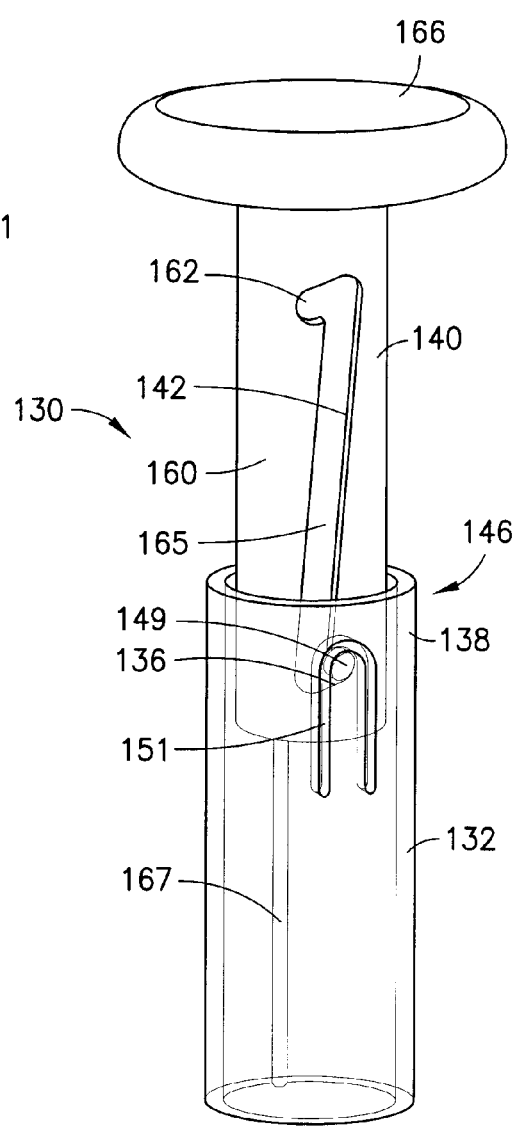
FIG. 6B is a front perspective view of the plunger rod of FIG. 6 in accordance with an embodiment of the present invention.
Figure 6A:
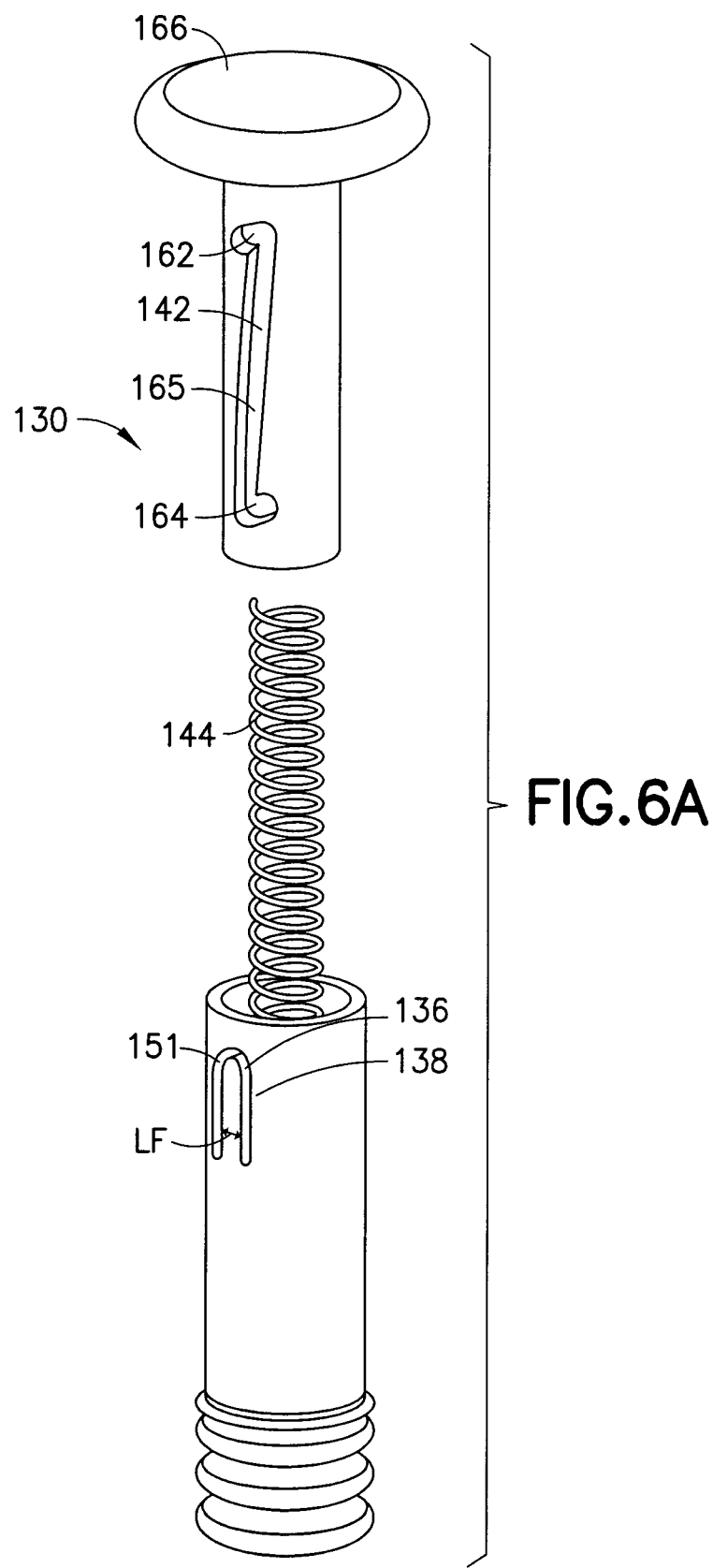
FIG. 6A is a partially expanded view of the syringe assembly of FIG. 6 in accordance with an embodiment of the present invention.

With continuing reference to FIGS. 1, 1A, 2, 2A-2B, 3, 4A-4B, and 5A-5B, the syringe assembly 10 includes a plunger rod, generally indicated as 30, associated with the stopper 22. The plunger rod 30 has an outer sleeve 32 having a distal end 34 interconnected to the stopper 22. The outer sleeve 32 includes an opening 36 extending through a sidewall portion 38. An inner sleeve 40 is mounted for telescopic movement within the outer sleeve 32. This inner sleeve 40 includes a longitudinally extending track 42. When assembled within the outer sleeve 32, at least a portion of the track 42 is in alignment with the opening 36 in the outer sleeve 32. The plunger rod 30 also includes a spring 44 mounted within and in association with the inner sleeve 40. The syringe assembly 10 further includes a holding mechanism, generally indicated as 46, associated with the plunger rod 30 and configured for cooperation with the inner sleeve 40 and outer sleeve 32, wherein an application of a distally directed force DF, as shown in FIG. 5A, to the plunger rod 30 causes the plunger rod 30 to transition from a collapsed pre-use position, as shown in FIGS. 1, 1A, 2, and 5A, to an extended ready-to-use position, as shown in FIG. 5B.

The distally directed force DF applied to the plunger rod causes relative movement between the inner sleeve 40 and outer sleeve 32 to release the spring 44 from a compressed position and allow the plunger rod 30 to extend to the ready-to-use position. As shown in FIGS. 1A and 5A, which show the pre-use position, the spring 44 is in the compressed position and the inner sleeve 40 is collapsed within the outer sleeve 32. As shown in FIG. 5B, the spring 44 is expanded and the inner sleeve 40 is extended out from the outer sleeve 32. Once the inner sleeve 40 is extended, it becomes locked in this position, as described in more detail below, and the plunger rod 30 and syringe 10 is ready for use.

Figure 2:
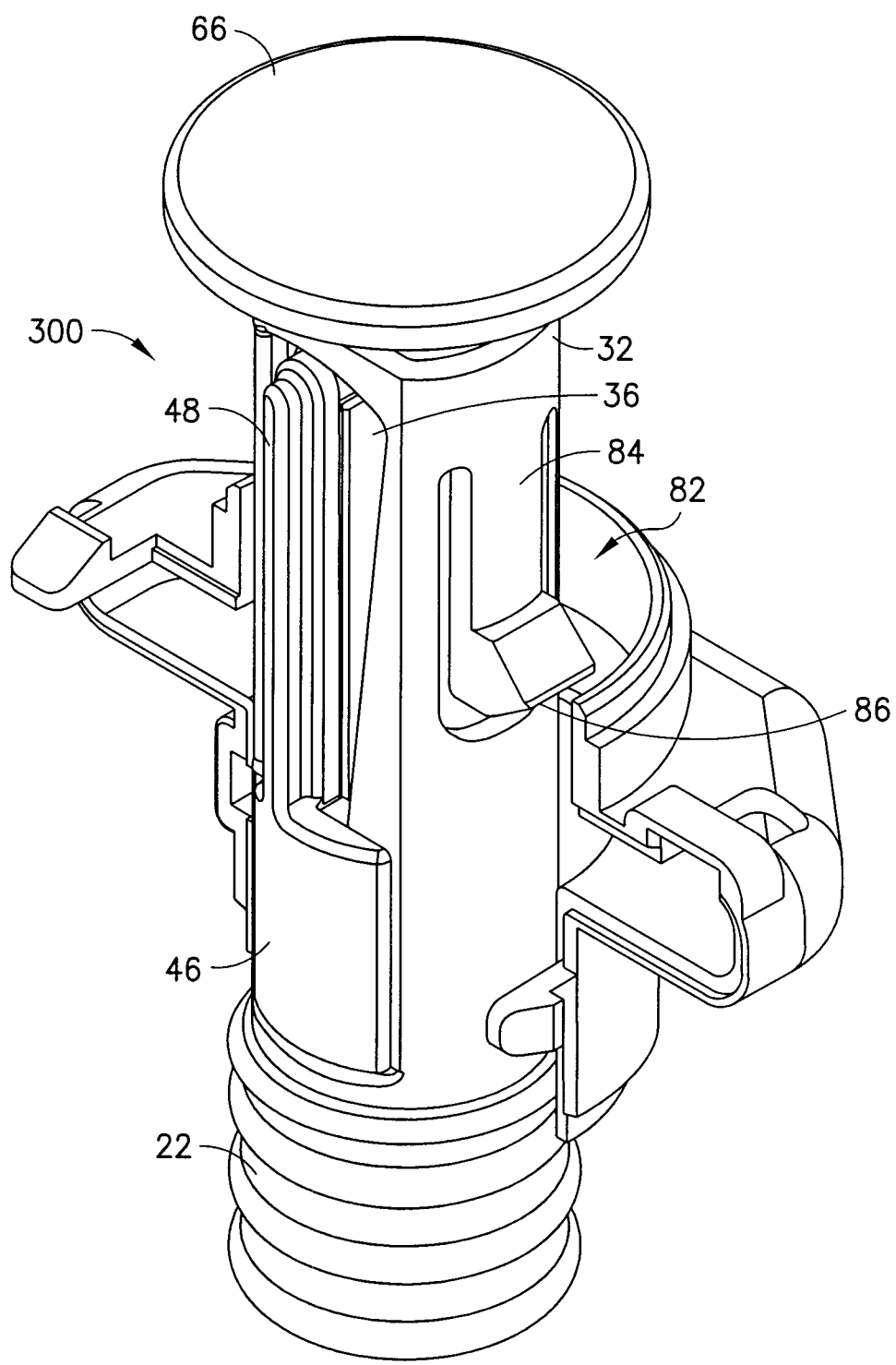
FIG. 2 is a front perspective view of the plunger rod of FIG. 1 including a portion of the syringe barrel in accordance with an embodiment of the present invention.

With particular reference to FIGS. 2, 2A, and 3, in certain configurations, the opening 36 in the outer sleeve 32 can have a longitudinally extending shape which extends along a longitudinal axis L, as shown in FIG. 3. The holding mechanism 46, associated with the outer sleeve 32, can include a flexible finger 48 that bisects the opening into a first open portion 50 and a second open portion 52. In can be appreciated that the holding mechanism 46 can be a separate member, including a base portion 58, and the flexible finger 48 that is secured to the outer sleeve 32 such as with a mechanical attachment member, adhesive, fusing, and the like, or the holding mechanism 46 can be integrally formed with the outer sleeve 32.

The longitudinally extending track 42 in the inner sleeve 40 can extend through a sidewall portion 60 of the inner sleeve 40 and can include a first stop 62 having an inclined surface 72, a second stop 64, and a longitudinal portion 65 extending between the first stop 62 and the second stop 64.

In operation, the flexible finger 48 is configured for cooperation with the opening 36 in the outer sleeve 32 and with the track 42 in the inner sleeve 40. A distally directed force DF applied to the inner sleeve 40, such as by the application of a downward force from the user to a thumb press 66 of the plunger rod 30, causes relative movement between the flexible finger 48 and the track 42 to release the spring 44 from the compressed position and allow the inner sleeve 40 of the plunger rod 30 to transition from the collapsed pre-use position to the extended ready-to-use position. It can be appreciated that the thumb press 66 can have a roughened or serrated surface, as is known in the art, to provide a frictional surface for assisting the user in movement or actuation of the plunger rod.

With particular reference to FIGS. 1A, 2A, and 3, the flexible finger 48 of the holding mechanism 46 can include a laterally extending member 68, such as in the form of a finger, that extends in a lateral direction, with respect to the longitudinal length of the flexible finger 48 and into a barrel or interior 70 of the outer sleeve 32. When the inner sleeve 40 is telescopically arranged with the outer sleeve 32, the finger 48 extends into the track 42 of the inner sleeve 40. When in the collapsed, pre-use position, this laterally extending member 68 is contained within the first stop 62. The application of a distally directed force to the inner sleeve 40 of the plunger rod 30 causes the laterally extending member 68 to interact with the inclined surface 72 of the first stop 62 and ride along this surface 72. This interaction then causes the flexible finger 48 to flex in a lateral direction LF, as shown in FIG. 2A, which allows the laterally extending member 68 to become disengaged from the first stop 62 and to enter into the longitudinal portion 65 of the track 42 in the inner sleeve 40. Once the laterally extending member 68 is located within the longitudinal portion 65 of the track, the inner sleeve 40 and the outer sleeve 32 are no longer locked together and the spring 44, associated with the inner sleeve 40, is released. It can be appreciated that the spring 44 can be associated with any internal portion of the inner sleeve 40, such as shown by 74 in FIGS. 5A and 5B, so that once compression force on the spring 44 is released, the spring 44 is biased so that it expands and forces the inner sleeve 40 to move in a proximal direction with respect to the distal end 14 of the syringe assembly 10 so that the inner sleeve 40 extends out from the outer sleeve 32, placing the plunger rod 30 in the extended, ready-to-use position.

Upon release and expansion of the spring 44, the laterally extending member 68 moves along the longitudinal portion 65 of the longitudinally extending track 42 and locks in the second stop 64 of the inner sleeve 40 to maintain the inner sleeve 40 and plunger rod 30 in the ready-to-use position.

According to a further aspect of the syringe assembly 10 of the invention and shown in FIGS. 4A and 4B, the inner sleeve 40 can include a locking finger 76 which, in addition to the locking achieved by the longitudinal portion 65 and the second stop 64, provides additional locking of the inner sleeve 40 within the outer sleeve 32 in the extended position. According to one embodiment, the locking finger 76 is configured for cooperating with an aperture 78 in the outer sleeve 32 to lock the plunger rod 30 in the extended ready-to-use position. It can be appreciated that the locking finger 76 can be located at a distal end 79 of a flexible member 80. A space 81 can be provided behind this flexible member 80 in order to allow the flexible member 80 to flex in an inward and outward direction with respect to the longitudinal centerline L of the syringe assembly 10 to enable the locking finger 76 to engage within the aperture 78. This locking arrangement also prevents pull-out of the inner sleeve 40 from the outer sleeve 32.

According to yet another aspect of the invention, as shown in FIGS. 1, 2, 3, and 5A-5B, the syringe assembly 10 can also include a stop member, generally indicated as 82, associated with the outer sleeve 32 and configured to cooperate with the syringe barrel 12 to limit movement of the outer sleeve 32 into the syringe barrel 12 upon the application of the distally directed force DF to the plunger rod 30.

According to one embodiment, this feature can comprise a flex finger 84 having a ramped portion 86 at one end thereof that prevents the application of a partial dose from a pre-filled syringe 10 as it limits or prevents the depression of the outer sleeve 32 into the syringe barrel 12 prior to desired use of the syringe assembly, i.e., until extension of the inner sleeve 40 with respect to the outer sleeve 32. In operation and with particular reference to FIG. 5A, when the inner sleeve 40 is in the collapsed position, a sidewall portion 88 of the inner sleeve 40 supports or applies a supporting surface against the stop member 82 and, should a distally directed force be applied to the plunger rod 30, the ramp portion 86 will engage against a top surface 90 of the flange 21 of the syringe barrel to prevent movement of the plunger rod 30 into the syringe barrel 12 and to prevent the application of a partial dose of the syringe contents. Once the inner sleeve 40 is extended with respect to the outer sleeve 32, the sidewall portion 88 of the inner sleeve 40 no longer provides a supporting surface against the stop member 82. This will allow the flex finger 84 to flex inward with respect to the longitudinal centerline L of the syringe assembly 10. Accordingly, the application of a distally directed force to the plunger rod 30 to expel the syringe contents will cause the plunger rod 30 to move into the syringe barrel and, when the ramped portion 86 of the flex finger 84 contacts the top surface 90 of the flange 21, the flex finger 84 can flex in an inward direction, to allow the outer sleeve 32 to enter into the syringe barrel 12.

Reference is now made to FIGS. 6 and 6A-6B, wherein a syringe assembly, generally indicated as 100, includes a spring actuated plunger rod according to another embodiment of the invention. The syringe assembly 100 is similar to syringe assembly 10, as discussed in detail above and includes a first or distal end 114, a second or proximal end 116, and a sidewall 118 extending between the distal end 114 and proximal end 116 defining an interior chamber 120 of a syringe barrel 112. A stopper 122 is disposed within the chamber 120 of the syringe barrel 112. The syringe barrel 112 may include an outwardly extending flange 121 about at least a portion of the proximal end 116. The flange 121 may be configured for easy grasping by a medical practitioner. The syringe assembly 100 can also include a tip cap 154.

With continuing reference to FIGS. 6 and 6A-6B, a plunger rod assembly 130 includes an outer sleeve 132 and an inner sleeve 140 telescopically mounted within the outer sleeve 132. The outer sleeve 132 is associated with the stopper 122. The outer sleeve 132 includes an opening 136 extending through a sidewall portion 138. The inner sleeve 140 includes a longitudinally extending track 142, such as a Z-shaped member that extends through a sidewall portion 160 of the inner sleeve 140. When assembled within the outer sleeve 132, at least a portion of the track 142 is in alignment with the opening 136 in the outer sleeve 132. The plunger rod assembly 130 also includes a spring 144 mounted within and in association with the inner sleeve 140. The syringe assembly 100 further includes a holding mechanism, generally indicated as 146 associated with the plunger rod assembly 130 and configured for cooperation with the inner sleeve 140 and outer sleeve 132, wherein an application of a distally directed force DF, as shown in FIG. 6, to the plunger rod assembly 130 causes the plunger rod assembly 130 to transition from a collapsed pre-use position, as shown in FIG. 6, to an extended ready-to-use position, as shown in FIG. 6B.

In this configuration, the holding mechanism 146 can comprise a spring finger 149 and a U-shaped locking member 151 cooperating with the outer sleeve 132 and the longitudinally extending track 142 of the inner sleeve 140. The longitudinally extending track 142 can include a first stop 162 for containing the spring finger 149 when the inner sleeve 140 is in the collapsed position, and a second stop 164 for containing the spring finger 149 and locking the inner sleeve 140 in place once the inner sleeve 140 is extended from the outer sleeve 132 in the ready-to-use position. The U-shaped locking member 151 also prevents pull-out of the inner sleeve 140 from the outer sleeve 132. A longitudinal portion 165 extends between the first stop 162 and the second stop 164 through which the spring finger 149 moves through during expansion of the spring 144 and during transitioning of the plunger rod assembly 130 from the collapsed, pre-use position to the extended ready-to-use position. The spring finger 149 is configured to laterally flex LF in two directions, as shown in FIG. 6A to enable it to flex in and out of the first stop 162 and the second stop 164.

It can be appreciated that the syringe assemblies 10 and 100 can include an alignment member associated with at least one of the inner sleeve 40, 140 and the outer sleeve 32, 132 to prevent relative rotation of the inner sleeve 40, 140 with respect to the outer sleeve 32, 132. According to one design as illustrated in FIG. 6B, this alignment member comprise a keyed track 167 in the outer sleeve 132.

Figure 7:
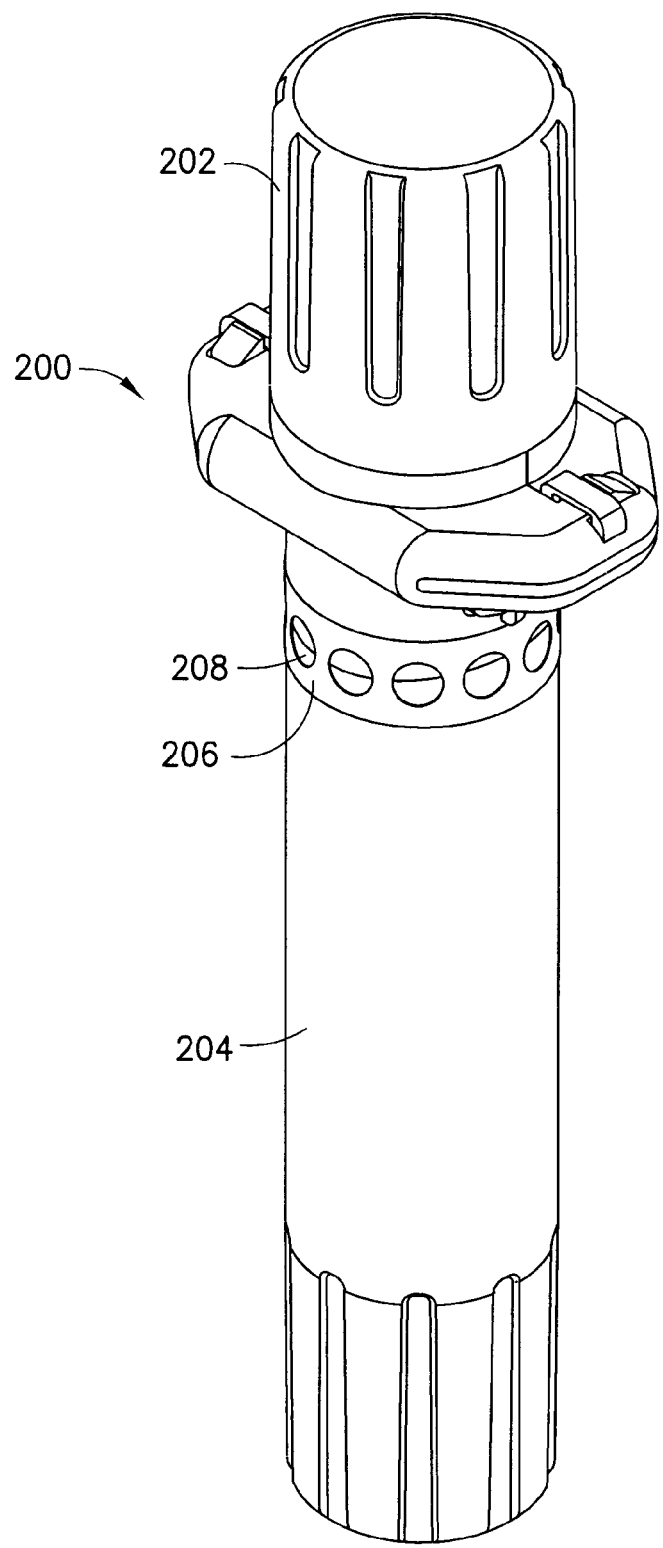
FIG. 7 is a front perspective view of the packaging arrangement for a syringe assembly having a spring action plunger rod in accordance with an embodiment of the present invention.

Reference is now made to FIG. 7 which shows a packaging assembly, generally indicated as 200, for use with a pre-filled syringe assembly 10, 100 having a spring released plunger rod 30, 130 in accordance with an embodiment of the present invention. It can be appreciated that this packaging assembly 200 can be used with either type of syringe assembly 10, 100, as discussed in detail above. The packaging assembly 200 includes a cap 202 configured for covering the plunger rod 30, 130, and a cover 204 molded about the syringe barrel 12, 112 and tip cap 54, 154. The cover 204 can be a tamper-indicating label, as shown at 206, and can be of a design known in the art and can include a frangible or perforated portion 208 for ease of removal from the syringe assembly 10, 100. This frangible portion can include markings, as are known in the art, to indicate if any tampering has occurred. One type of label is a shrink-wrap type label which can encompass the tip cap 54, 154 and a portion of the syringe barrel 12, 112 and/or cap 202. The cap 202 can comprise a rigid member configured to prevent the application of a distally directed force on the plunger rod 30, 130 until the cap 202 is removed.

Reference is now made to FIGS. 8A-8C which show a packaging assembly, generally indicated as 300, for use with a pre-filled syringe assembly 10, 100 having a spring released plunger rod 30, 130 in accordance with another embodiment of the present invention. This packaging assembly 300 can also be used with either type of syringe assembly 10, 100, as discussed in detail above. The packaging assembly 300 can include a tear tab 302 positioned about a portion of the plunger rod 30, 130 at a location between a plunger rod thumb press 66, 166 and the syringe barrel flange 21, 121. The tear tab 302 is configured to prevent distal movement of the inner sleeve 40, 140 of the plunger rod 30, 130 resulting in an inadvertent release of the spring 44, 144 and extension of the inner sleeve 40, 140. A cover 304 can be molded about a syringe barrel 12, 112 and tip cap 54, 154. The cover 304 can include a tamper-indicating member, such as a colored label 306, as discussed in detail above, and can include a frangible or perforated portion to assist in the removal of the cover 304 from about the syringe barrel 12, 112 and tip cap 54, 154. The tear tab 302 can include a grasping portion 308, including a roughened portion, to assist in removal of the tear tab 302 from about the plunger rod 30, 130. In operation, the user can remove the tear tab 302, as shown in FIGS. 8A and 8B and remove the cover 304. The syringe assembly 10, 100 is now ready for activation of the plunger rod 30, 130 and subsequent use.

It can be appreciated that the syringe assembly embodiments disclosed above result in a syringe assembly having a reduced footprint which is desirable in the packaging of the syringe assemblies as it requires less packaging. This reduced footprint provides for syringe assemblies having consistently sized profiles which allow for easy stacking and require less storage space, both of these features being desirable in a controlled storage environment.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention.

The invention claimed is:

1. A syringe assembly comprising:
    a syringe barrel having a first end, a second end, and a sidewall extending between the first end and the second end defining a chamber;
    a stopper disposed within the chamber of the syringe barrel;
    a plunger rod associated with the stopper, the plunger rod comprising:
        an outer sleeve having a distal end interconnected to the stopper, the outer sleeve comprising a sidewall portion defining an opening therein;
        an inner sleeve disposed within the outer sleeve, the inner sleeve including a longitudinally extending track, at least a portion of the track being in alignment with the opening in the outer sleeve, wherein the inner sleeve is adapted for telescopic movement with respect to the outer sleeve; and
        a spring mounted in association with the inner sleeve; and
    a holding mechanism arranged on the outer sleeve and configured to cooperate with the track in the inner sleeve, wherein the holding mechanism holds the plunger rod in a pre-use position wherein the spring is held in a compressed position and relative movement between the inner sleeve and the outer sleeve causes the spring to be released from the compressed position and the plunger rod to transition from the collapsed pre-use position to an extended ready-to-use position.

2. The syringe assembly of claim 1, wherein the opening in the outer sleeve comprises a longitudinally extending opening and the holding mechanism comprises a flexible finger associated with the longitudinally extending opening, the flexible finger configured for cooperation with the opening in the outer sleeve and with the track in the inner sleeve, and wherein a distally directed force applied to the inner sleeve causes relative movement between the flexible finger and the track to release the spring from the compressed position and allow the inner sleeve of the plunger rod to transition from the collapsed pre-use position to the extended ready-to-use position.

3. The syringe assembly of claim 2, wherein the longitudinally extending track extends through a sidewall portion of the inner sleeve and the track includes a first stop and a second stop.

4. The syringe assembly of claim 3, wherein the flexible finger includes a laterally extending member that extends through the opening in the outer sleeve and the track in the inner sleeve, and wherein the distally directed force causes disengagement of the laterally extending member of the flexible finger from the first stop and release of the spring.

5. The syringe assembly of claim 4, wherein upon release of the spring, the laterally extending member moves along the longitudinally extending track and locks in the second stop to maintain the inner sleeve in the ready-to-use position.

6. The syringe assembly of claim 5, wherein the flexible finger is configured to flex in a lateral direction with respect to the longitudinally extending track and the opening in the outer sleeve to allow the laterally extending member to disengage from the first stop and engage the second stop upon release and expansion of the spring.

7. The syringe assembly of claim 1, wherein the inner sleeve includes a locking finger configured for cooperating with an aperture in the outer sleeve for locking the plunger rod in the extended ready-to-use position and for preventing pull-out of the inner sleeve from the outer sleeve.

8. The syringe assembly of claim 1, wherein the holding mechanism is secured to the outer sleeve.

9. The syringe assembly of claim 1, further comprising an alignment member associated with at least one of the inner sleeve and the outer sleeve to prevent relative rotation of the inner sleeve with respect to the outer sleeve.

10. The syringe assembly of claim 9, wherein the alignment member comprises a keyed track.

11. The syringe assembly of claim 1, wherein the holding mechanism comprises a spring finger and a U-shaped locking member cooperating with the outer sleeve and the longitudinally extending track of the inner sleeve.

12. The syringe assembly of claim 1, further comprising a medication or drug disposed within the syringe barrel.

13. A spring released plunger rod assembly comprising:
    an outer sleeve having a first end configured for interconnecting to a stopper, the outer sleeve including an opening extending through a sidewall portion;
    an inner sleeve disposed within the outer sleeve and mounted for telescopic movement with respect to the outer sleeve;
    a spring mounted in association with the inner sleeve;
    a longitudinally extending track associated with the inner sleeve; and
    a holding mechanism arranged on the outer sleeve and configured to cooperate with the track of the inner sleeve, wherein the holding mechanism holds the plunger rod in a pre-use position wherein the spring is held in a compressed position and relative movement between the outer sleeve and the inner sleeve causes the spring to be released from the compressed position and the plunger rod to transition from the collapsed pre-use position to an extended ready-to-use position.

14. The spring released plunger rod assembly of claim 13, wherein the holding mechanism comprises a flexible finger, the flexible finger configured for cooperation with the opening in the outer sleeve and with the track in the inner sleeve, and wherein a distally directed force applied to the inner sleeve causes relative movement between the flexible finger and the track to release the spring from a compressed position and to allow the inner sleeve of the plunger rod assembly to transition from the collapsed pre-use position to the extended ready-to-use position.

15. The spring release plunger rod assembly of claim 14, wherein the longitudinally extending track extends through a sidewall portion of the inner sleeve and includes a first stop and a second stop, and wherein the flexible finger includes a laterally extending member and the distally directed force causes disengagement of the laterally extending member from the first stop to release the spring.

16. The spring release plunger rod assembly of claim 13, wherein the inner sleeve includes a locking finger configured for cooperating with an aperture in the outer sleeve for locking the plunger rod in the extended ready-to-use position and for preventing pull-out of the inner sleeve from the outer sleeve.

17. The spring release plunger rod assembly of claim 13, further comprising a stop member associated with the outer sleeve and configured to cooperate with a syringe barrel to limit movement of the outer sleeve into the syringe barrel upon the application of a distally directed force to the plunger rod.

18. The spring release plunger rod assembly of claim 13, wherein the holding mechanism comprises a spring finger and a U-shaped locking member cooperating with the outer sleeve and the longitudinally extending track of the inner sleeve.

* * * * *